(12) United States Patent
Nørgaard

(10) Patent No.: US 10,091,595 B2
(45) Date of Patent: Oct. 2, 2018

(54) CORRECTION OF ANALYTICAL IMPEDANCES IN ACOUSTIC THEVENIN CALIBRATION OF DIAGNOSTIC PROBES AND HEARING AIDS

(71) Applicant: Interacoustics A/S, Middelfart (DK)

(72) Inventor: Kren Rahbek Nørgaard, Middelfart (DK)

(73) Assignee: INTERACOUSTICS A/S, Middelfart (DK)

( * ) Notice: Subject to any disclaimer, the term of this patent is extended or adjusted under 35 U.S.C. 154(b) by 154 days.

(21) Appl. No.: 15/179,282

(22) Filed: Jun. 10, 2016

(65) Prior Publication Data

US 2016/0366526 A1 Dec. 15, 2016

(30) Foreign Application Priority Data

Jun. 12, 2015 (EP) .................................... 15171935

(51) Int. Cl.
| | |
|---|---|
| *H04R 25/00* | (2006.01) |
| *A61B 5/12* | (2006.01) |
| *G01H 15/00* | (2006.01) |
| *G01H 17/00* | (2006.01) |

(52) U.S. Cl.
CPC ............... *H04R 25/70* (2013.01); *A61B 5/12* (2013.01); *G01H 15/00* (2013.01); *G01H 17/00* (2013.01); *H04R 25/30* (2013.01); *A61B 2560/0223* (2013.01)

(58) Field of Classification Search
CPC .......... A61B 5/12; G01H 15/00; G01H 17/00; H04R 25/30
See application file for complete search history.

(56) References Cited

U.S. PATENT DOCUMENTS 5,651,371 A 7/1997 Keefe

OTHER PUBLICATIONS

Brass, David et al., "The effect of the evanescent wave upon acoustic measurements in the human ear canal", The Journal of the Acoustical Society of America, Apr. 1. 1997, vol. 101, No. 4, pp. 2164-2175.

(Continued)

*Primary Examiner* — Brian Ensey
(74) *Attorney, Agent, or Firm* — Birch, Stewart, Kolasch & Birch, LLP

(57) ABSTRACT

A method for carrying out acoustic Thevenin calibration of probes or hearing aids comprises presenting a plurality of different acoustic loads, one acoustic load at a time, to the output of the probe or hearing aid, the source characteristic of which is to be determined. Each of the acoustic loads is characterized by a known acoustic input impedance and an additional frequency dependent complex correction factor ΔZ(f). By applying the method according to the present disclosure the relationship between the sound pressure and the volume velocity at the input of the acoustic load generated by the probe can be determined for a plurality of frequencies, thereby obtaining the substantially correct source characteristic of the probe or a hearing aid. Specifically the acoustic loads are the input impedance of respective waveguides or other suitable cavities, and the known acoustic input impedances are determined analytically. The correction factors are adjusted individually for each waveguide or cavity, for instance in an iterative process.

13 Claims, 4 Drawing Sheets

(56) References Cited

OTHER PUBLICATIONS

Fletcher, N. H. et al., "Acoustic impedance measurements—correction for probe geometry mismatch", The Journal of the Acoustical Society of America, May 1, 2005, vol. 117, No. 5, pp. 2889-2895.

Lewis, James D. et al., "Comparison of in-situ calibration methods for quantifying input to the middle ear", The Journal of the Acoustical Society of America, Dec. 1, 2009, vol. 126, No. 6, pp. 3114-3124.

CORRECTION OF ANALYTICAL IMPEDANCES IN ACOUSTIC THEVENIN CALIBRATION OF DIAGNOSTIC PROBES AND HEARING AIDS

FIELD

The present disclosure relates to acoustic load impedances used for calibration of probes that are applied to determine acoustic source characteristics. More specifically, the disclosure relates to determining the acoustic source characteristics of diagnostic probes and hearing aids.

BACKGROUND

Acoustic Thevenin calibration is a method used to determine the equivalent Thevenin parameters of acoustic probes used in hearing diagnostics and hearing aids (HA). Thevenin calibration is an important calibration step to perform when measuring acoustics in for example hearing diagnostic applications, this being due to the high accuracy requirements needed when performing hearing diagnostics to evaluate a potential hearing loss. Therefore, the acoustic probes used in at least hearing diagnostic applications should be calibrated prior to the actual diagnostic measurements.

Acoustic Thevenin calibration determines the source characteristics (i.e. the source pressure and the source impedance) of the acoustic probe to be used for measurements in an object, such as the ear canal of a test-person. Finding the source characteristics of the acoustic probe from a calibration step, makes it possible to measure any load impedance applied to the probe or HA. Thus, a Thevenin calibration of an acoustic probe is a calibration step, which is usually performed prior to the actual measurements in an object, such as in the ear canal of a user, for which the impedance should be measured for the purpose of e.g. providing a diagnosis. Similarly, within other acoustic applications, such as musical acoustics, a Thevenin calibration may also be applied to the acoustical probes prior to the measurement of e.g. impedance of an acoustic instrument, such as a musical instrument, to obtain a performance characteristic of the acoustic instrument.

Accordingly, it is generally appreciated within the field of measuring the acoustic characteristics of an object to perform a Thevenin calibration of acoustic probes prior to the actual measurements of an object of interest.

The Thevenin calibration method is based on presenting a number of reference loads to the probe or HA, whose impedances are known or can be calculated analytically. Typically, these loads are hard walled cylindrical waveguides of different lengths. The response in each waveguide is then used to find the Thevenin parameters (i.e. the source characteristics of the probe) using a least squares fit (i.e. solving the least square fit equation to find the source pressure and the source impedance).

This calibration procedure is in practice very sensitive to the analytical or assumed plane wave impedance of the waveguide. In reality, the true impedance (i.e. the load impedance measured) as seen by the probe (or HA), differs from the analytical impedance due to phenomena associated with the sound transitioning from a narrow delivery orifice (such as a tube or an annular slit) in the probe (or HA) to a wider waveguide. The sound pressure is measured in close proximity to the delivery tube, introducing an error in the measured frequency response function.

Within the field of acoustic applications, it is generally known that such errors introduced are caused by a geometrical mismatch between the acoustic probe and the load applied thereto, and which are at least related to evanescent modes. Thus, there has been a general need to avoid the effects of at least evanescent modes during impedance measurements of an object of interest.

One approach used for avoiding evanescent modes when measuring the acoustic impedance of a real ear set-up (i.e. an acoustic probe tube being inserted into the ear canal of a test-subject) has been focused on sufficiently attenuating any localized, non-propagating acoustic field caused by evanescent modes. This has been achieved by restricting the frequency content of the external stimuli or by drawing the probe microphone, recording the response in the test-object, slightly beyond the plane of the probe transducer emitting the sound stimuli into the test-object. In other words, one method to compensate for evanescent modes is by protruding the measurement microphone of the acoustic probe a given distance beyond the plane of the probe tip, whereby the probe response is significantly less affected by evanescent modes. Main drawback with this approach is that the excess waveguide between the source outlet and microphone inlet is included in the source characteristics rendering the calibration invalid when inserted into a waveguide of different dimensions.

Other methods focusing on compensating impedance measurements for the errors introduced by a geometrical mismatch are aiming at applying a correction factor to the resulting impedance measurements performed on a test-object and subsequent to any probe calibration procedure.

As previously elaborated on, it is known within the art to perform acoustic input impedance measurements of acoustic waveguides using a traditional impedance probe comprising an annular sound emitting slit assumed to provide a constant volume velocity. Furthermore, the acoustic probes used to measure the input impedances are, as already explained, in a first step, calibrated prior to the real impedance measurements, so as to obtain the Thevenin parameters (i.e. source characteristics) of the acoustic probe used for the impedance measurements. In a second subsequent step, the calibrated acoustic probe is inserted into the test-object, device, another waveguide or instrument, of which the impedance should be measured. As previously described real impedance measurements, whether being performed in e.g. an ear canal or a musical application, may also experience errors related to geometrical mismatch between the acoustic probe and the test-object.

In addition to the already described prior art method, other suggested methods for compensating for such errors in the measured impedance subsequently to calibration of the acoustic probe used for the measurement, therefore includes a correction of the obtained impedance measurement results. Such corrections are suggested to be made by visual inspection of the measured impedance, and includes an imaginary, frequency proportional correction factor, which is adjusted such that impedance minima are placed half-way between two subsequent maxima in the impedance measurements. Furthermore, a real correction factor proportional to the square root of frequency is adjusted such that the envelope of impedance minima is equal to the envelope of impedance maxima. This method of correcting for a geometrical mismatch entails some constraints to the subsequent measurement with the acoustic probes. When finding the correction factors of the calibrated acoustic probe, this is done in a tube having a specific geometry matching that of the object to be measured. This entails the constraint that the measurement device to be measured in a final impedance measurement should substantially be coupled to the acoustic probe through tubes having the same diameter as the tube which was used for estimating the correction factors. Thus, the correction factors related to the geometrical mismatch found by this method can only be used on a limited number of actual devices having substantial the same geometry as the one assumed during the correction measurements in front of the probe.

As is apparent, the known methods are not related to determining the source characteristics of the probe, which characteristics are determined in a previous calibration step in a traditional way by placing the annular probe in a semi-infinite waveguide. The calibration is possible using only a single load since this probe is assumed a constant volume velocity source. This is equivalent to assuming an infinite source impedance in the Thevenin parameters. Such calibration will be affected by evanescent modes, but since no impedance minima are present in the impedance spectrum of a non-reflecting load the relative influence will be negligible.

Furthermore, the known methods are suggesting compensating for evanescent modes subsequent to the calibration of the acoustic probes which should be used for impedance measurements, however entailing some limitations to the subsequent actual device measurements. Thus, potential errors introduced already in the calibration of the acoustic probe are not accounted for in current methods.

Therefore, there is a need to provide a solution that removes or at least reduces the calibration errors associated with the above mentioned geometric mismatch between the probe and the given waveguide.

SUMMARY OF THE DISCLOSURE

This and other objects are achieved by providing a calibration method, which accounts for any geometrical mismatch of any load applied to the acoustic probe (such as a device to be tested) during calibration of the acoustic probe that should be used for subsequent impedance measurements on devices of interest.

That is, according to a first aspect of the present disclosure, initially described problems are solved or at least reduced by the provision of a method for carrying out acoustic Thevenin calibration of probes or hearing aids, where the method comprises the steps of presenting a plurality of different acoustic loads, one acoustic load at a time, to the output of the probe or hearing aid, the source characteristics of which is to be determined. Each of the acoustic loads are according to the present disclosure characterized by a known acoustic input impedance (that for instance can be calculated analytically or determined a priory based on suitable measurements) and an additional frequency dependent complex correction factor $\Delta Z(f)$. By applying this corrected input impedance of the acoustic load, the relationship (i.e. the ratio) between the sound pressure at the probe microphone and the volume velocity injected by the probe can be determined correctly for a plurality of frequencies, thereby obtaining the desired substantially correct source characteristics of the probe or of a hearing aid.

With such method, it is achieved that the errors introduced to the probe response from a geometrical mismatch are accounted for already at the Thevenin calibration of the acoustic probe in a step prior to the actual impedance measurement of a device. Thus, a subsequent impedance measurement carried out using the calibrated probe will include the potential effects of evanescent modes and flow losses that were compensated during calibration.

In more detail, the traditional Thevenin calibration method is based on presenting a number of different acoustic loads (typically waveguides of different lengths) to the acoustic probe. The impedances of these acoustic loads are known or can be calculated analytically. These acoustic loads will in the following be termed "analytical impedances" or "reference impedances". The correction factors described throughout this disclosure should be understood to be applied directly to each of the acoustic loads used in the Thevenin calibration step of the acoustic probe.

It should be noted that, although the acoustic loads in the following are exemplified by acoustic waveguides, the acoustic loads according to the present disclosure could be any cavity of any dimensions and geometry that would render such cavities applicable in the method and devices according to the present disclosure.

In reality, the true impedance seen by the probe differs from the analytical plane wave impedance due to phenomena associated with the sound transitioning from a narrow orifice (for instance a tube or slit) in the probe or hearing aid to a wider waveguide. These phenomena are as previously described caused by a geometrical mismatch between the acoustic probe used for impedance measurements and the test-object (e.g. a load, a waveguide, ear canal or similar) in which the acoustic probe is inserted. This geometrical mismatch introduces errors in the measured impedance, usually seen as a displacement of the minima in the impedance curve, which are misaligned in view of the analytical impedance. Thus, when finding the source characteristics of the probe, i.e. the source pressure and the source impedance using a Thevenin calibration, the reference impedance (also denoted analytical or modeled impedance) should be corrected to take into account such mismatch in order to get an accurate subsequent impedance measurement of an acoustic load applied to the probes. Therefore, in the context of this disclosure the "substantially correct source characteristic of the probe" should be understood to be the source characteristics (i.e. sound pressure and volume velocity) which takes into account any errors introduced by a geometrical mismatch between the acoustic probe and the load applied thereto during calibration. Such Thevenin calibrated probe accounting for any geometrical mismatch correction factor according to the disclosure during calibration, may be used in a subsequent impedance measurement of a device, but now measuring the acoustic impedance having the effects induced by the geometry mismatch between the probe and acoustic load under investigation included in the measured impedance.

Accordingly, the errors introduced by this geometrical mismatch can be significantly reduced by applying a complex frequency dependent correction factor (or function) to the analytical impedances used in the method described herein. That is, the correction factor may be applied to any one of the analytical impedances of each of the loads used for the purposes of performing the Thevenin calibration. The complex correction factor can be expressed as:

$$\Delta Z(f) = \Delta Zre(f) + i\Delta Zim(f) \qquad (1)$$

The addition of the real part of the correction factor to the real part of the analytical impedance results in that the damping in impedance minima is changed, i.e. the Q-factor of the impedance minima is reduced or increased. The addition of the imaginary part of the correction factor to the imaginary part of the analytical impedance results in that the minima of the estimated impedance are shifted in frequency while the maxima are maintained.

The correction factor added to the real part of the analytical impedance seeks to add the effects that emerge from the velocity singularity that arises when sound travels around a sharp corner to the analytical impedance. This effect is primarily seen when sound pressure is measured very close to the sound outlet since the large gradients in the velocity field have to be balanced by an equivalent pressure drop in the momentum equation.

The imaginary correction factor seeks to add the effects of evanescent modes to the analytical impedance. Evanescent modes arise when sound transitions from a narrow to a wider waveguide as a spherical wave propagation superposition to the plane wave, travelling a short distance down the waveguide.

Such complex correction factor has in the prior art been added to the actual measured impedances as described previously in the background section and not as part of the Thevenin calibration of the acoustic probe used for said actual measurements. As previously elaborated on, this however entails at least the constraint that for further use of the found correction factors in a new impedance measurement, the substantially same geometry of the object to be measured should be ensured in order to get accurate impedance measurements. As described, this form of compensation for evanescent mode subsequent to Thevenin calibration of the acoustic probe is not related to the method described throughout this disclosure, and such correction would not take into account errors induced already in during calibration of the acoustic probe.

According to an embodiment of the disclosure the correction factors are adjusted individually for each waveguide in an iterative process to obtain the lowest possible error (being defined as the ability of the obtained Thevenin parameters to estimate the corrected reference impedances) to account for slight differences in insertion resulting in variation of correction factors for each waveguide. The number of iterative steps for the error to converge to a minimum is reduced by applying an initial value for both correction factors equal to an expected value for the specific probe and waveguide combination obtained from a previous calibration.

According to a first embodiment of the first aspect of the disclosure the above mentioned loads are the input impedance of respective acoustic waveguides. A non-limiting example of a waveguide that can be used according to the present disclosure is shown and described in the following detailed description.

According to a second embodiment of the first aspect of the disclosure, the known acoustic impedances are determined analytically.

According to a third embodiment of the first aspect of the disclosure the correction factors are adjusted individually for each load or waveguide in an iterative process, whereby the lowest possible error due to slight differences in insertion of the probe into the acoustic load resulting in variation of correction factors for each waveguide is obtained.

According to a fourth embodiment of the first aspect of the disclosure the number of iterative steps required for the error to converge to a minimum is reduced by applying an initial value for both correction factors equal to an expected value for the specific probe and waveguide combination obtained from a previous calibration.

According to a fifth embodiment of the present disclosure the frequency dependent complex correction factor $\Delta Z(f)$ is given by the expression:

$$\Delta Z(f) = \Delta Zre(f) + i\Delta Zim(f) \quad (2)$$

where:

$$\Delta Zre(f) = Cre\sqrt{f}$$

and $$\Delta Zim(f) = iCimf \quad (3)$$

According to a second aspect of the present disclosure there is provided a cavity for acoustic Thevenin calibration of diagnostic probes and hearing aids, where the cavity is provided with a probe insert configured for coupling the sound outlet of an acoustic probe or a hearing aid to the cavity. The acoustic input impedance as seen from the sound outlet from the acoustic probe is a combination of a known acoustic input impedance and an additional frequency dependent complex correction factor $\Delta Z(f)$ that is given by the expression:

$$\Delta Z(f) = \Delta Zre(f) + i\Delta Zim(f)$$

According to an embodiment of the second aspect of the present disclosure the cavity is a waveguide with a body portion comprising an inner substantially cylindrical channel of a given length and a given diameter, which channel at a first longitudinal end is terminated by a substantially acoustically rigid plate and at an opposite second longitudinal end is provided with a probe insert configured for coupling the sound outlet of a probe to the second longitudinal end of the channel.

According to an embodiment of the second aspect of the disclosure the frequency dependent complex correction factor is given by the expression:

$$\Delta Zre(f) = Cre\sqrt{f}$$

and $$\Delta Zim(f) = iCimf$$

where Cre and Cim are real constants, f is the frequency and i is the imaginary unit.

It is understood that although in some of the embodiments described and claimed in the present disclosure the real and imaginary parts of the frequency dependent complex correction factor are given by expression (3) above. The method and device according to the present disclosure are not limited to the application of this specific correction factor.

Compared to the original method (i.e. the prior art methods) where no correction factors are applied to the Thevenin calibration of the acoustic probes used for impedance measurements a much smoother and precise calibration is obtained. This is especially the case in and in the vicinity of the reference impedance minima where the correction factors constitute a relatively larger part of the impedance. The immediate advantage of this disclosure is, of course, a more precise diagnostic output of a probe (or HA). Furthermore, since the correction factors would typically scale with frequency, this disclosure seems crucial if a calibration at very high frequencies is desired. In recent years, some research has focused on deriving different parameters such as the ear canal area function and time domain reflectance from a single impedance measurement. The estimation of many of these parameters seems to take significant advantage of the increased calibration precision and ability to calibrate at higher frequencies. As a last point, the disclosure would theoretically allow for calibration of probes or hearing aids with a much more drastic geometry mismatch to the calibration waveguides than currently possible.

The typical use-case in relation to the disclosure for an acoustic probe is the conversion of measured acoustic impedance to power reflectance or absorbance in a diagnostic context, but could also include stimulus level estimation in distortion product otoacoustic emissions. For HA's, possible uses include middle ear function monitoring using absorbance and simplified HA fitting due to no probe microphone needed in proximity to the tympanic membrane.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 2(a) shows the magnitude of the impedance, FIG. 2(b) shows the phase of the impedance and FIG. 2(c) shows the absolute value of the relative error corresponding to each respective of the four applied waveguides;

DETAILED DESCRIPTION OF AN EXAMPLE EMBODIMENT OF THE DISCLOSURE

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the system and method are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

Figure 1:
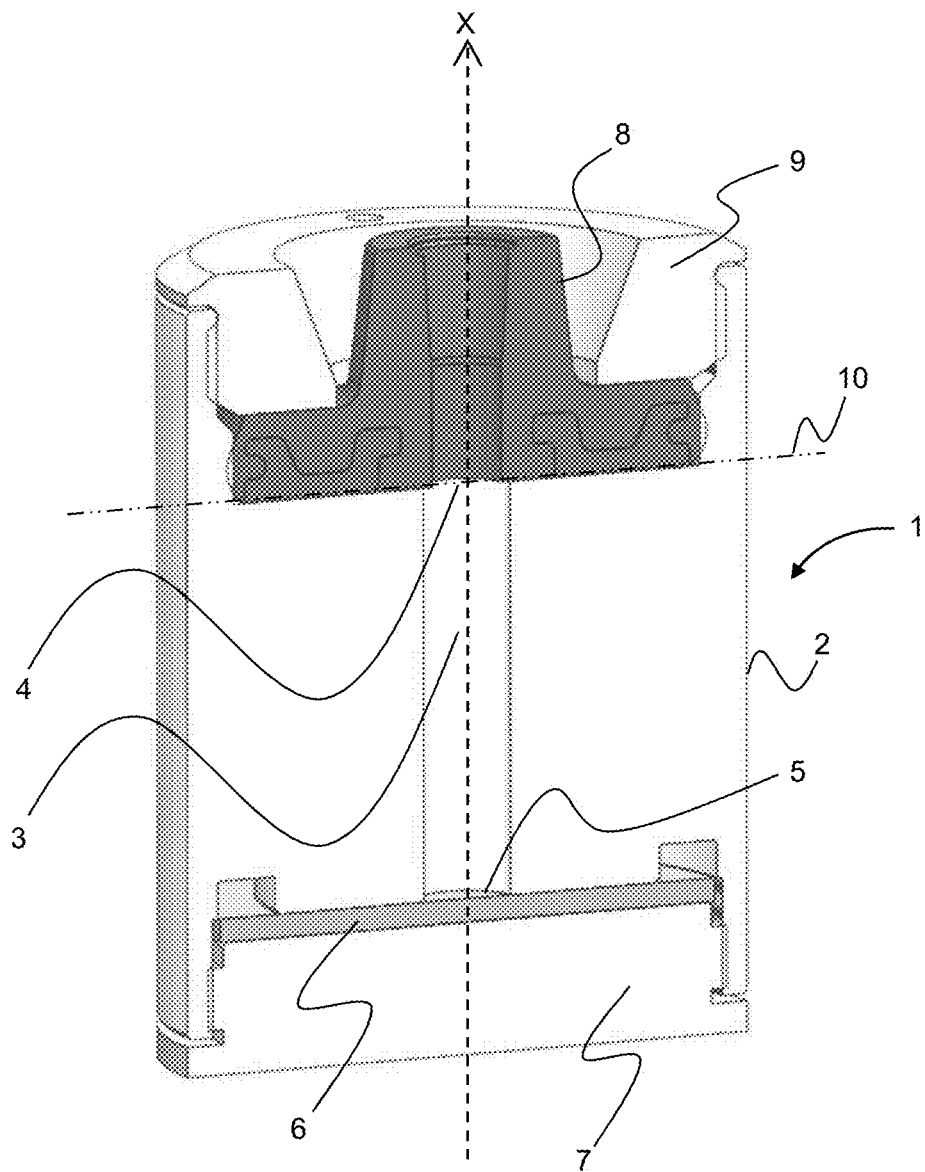
FIG. 1 shows a cross-sectional view of an exemplary embodiment of a calibration waveguide according to the disclosure comprising a probe insert (shown in dark colour) that is inserted into the cylindrical waveguide.

Referring to FIG. 1 there is shown a cross-sectional view of a calibration waveguide member according to an embodiment of the disclosure generally indicated by reference numeral 1. The waveguide comprises a cylindrical body portion 2 extending longitudinally along a longitudinal axis X. Inside the cylindrical body portion 2 there is provided a cavity 3 that constitutes the waveguide as such and that at one end 5 hereof is terminated by a substantially acoustically rigid plate 6 that is secured to the body portion 2 by a second threaded end portion 7. At the opposite longitudinal end 4 of the waveguide member 1 there is inserted a probe insert 8 that is made of a suitable resilient material, such as rubber. The probe insert 8 is secured to the body 2 of the waveguide member 1 by means of a first threaded end portion 9. And the proximal end of the probe insert defines the input plane 10 of the waveguide. The body portion 2 can be made of aluminium or another suitable material. An impedance measuring probe (not shown in FIG. 1) can be inserted in the probe insert 8. A typical probe for impedance measurements will comprise two sound conducting channels, one for emitting a sound signal from a suitable source into the waveguide 3 and one for conducting sound from the waveguide to a measuring microphone. The probe insert allows the tip of the probe, where the sound from the sound emitting source enters the waveguide and is picked up by the measuring microphone to be placed exactly flush with the input reference plane of the waveguide cavity 3.

It is important that the probe is placed correctly in each calibration waveguide. According to an embodiment of the method according to the disclosure there is used a set of four waveguides of lengths 1.2 cm, 1.45 cm, 1.75 cm, 2 cm, all having a diameter of 4 mm. To obtain a well-defined length of the waveguide, the probe must be placed exactly flush with the input plane 10 of the waveguide. This is achieved by the configuration shown in FIG. 1.

In the method according to the disclosure, each of the for example four waveguides are used in the Thevenin calibration of the acoustic probe, where at least one complex correction factor is applied to each of the reference impedances of the waveguides. Thus, in the present example at least four probe responses are used in a subsequent least squares fit error optimization to obtain the optimal source characteristic of the acoustic probe used for the measurements. In this way, the acoustic probe is calibrated prior to the actual impedance measurements on a device of interest, so as to account for any errors in the reference impedances, which are caused by at least a substantial range of geometrical mismatches between the acoustic probe and the load applied thereto.

Figure 2:
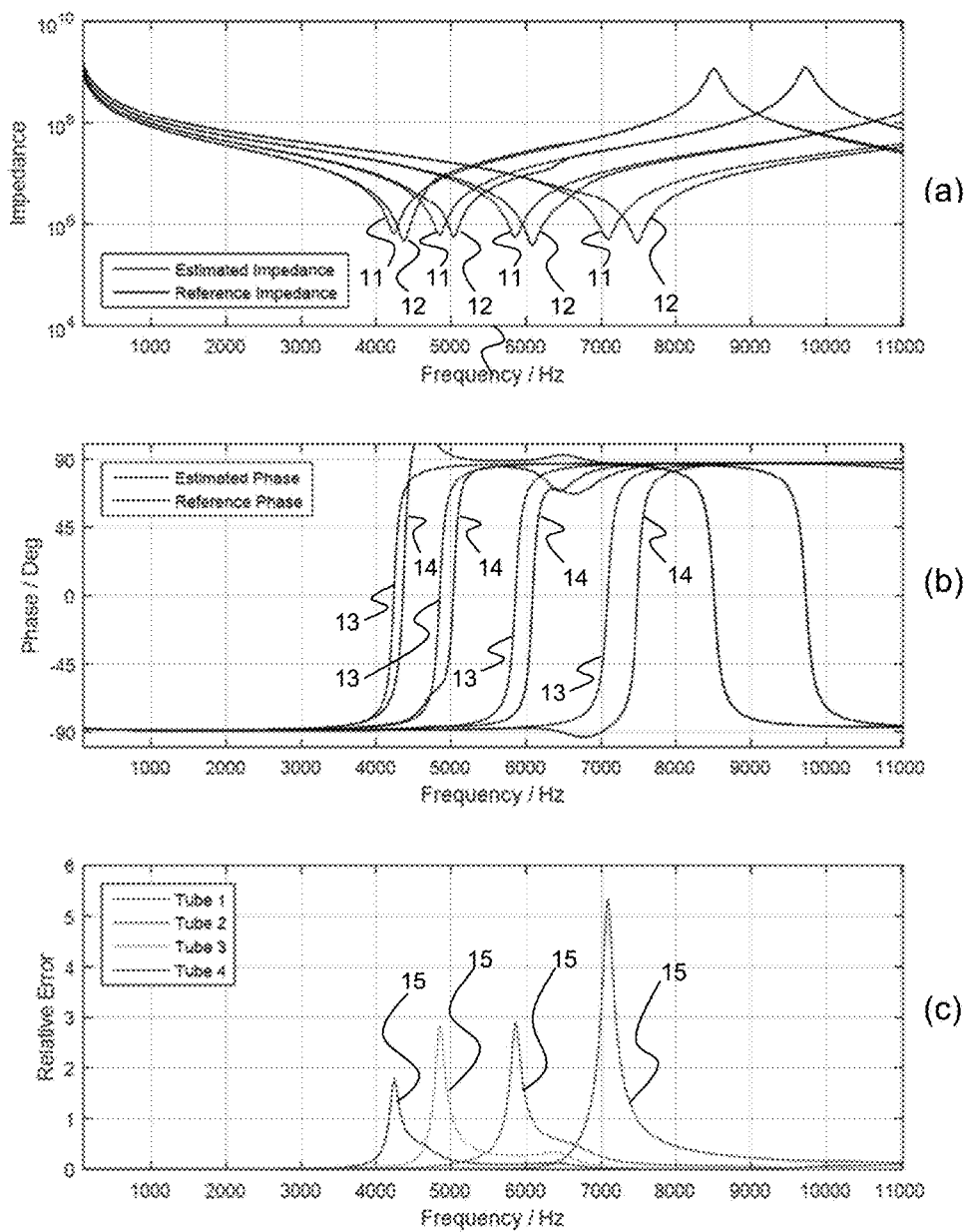
FIG. 2 shows results of a calibration without any correction values applied where
Figure 3:
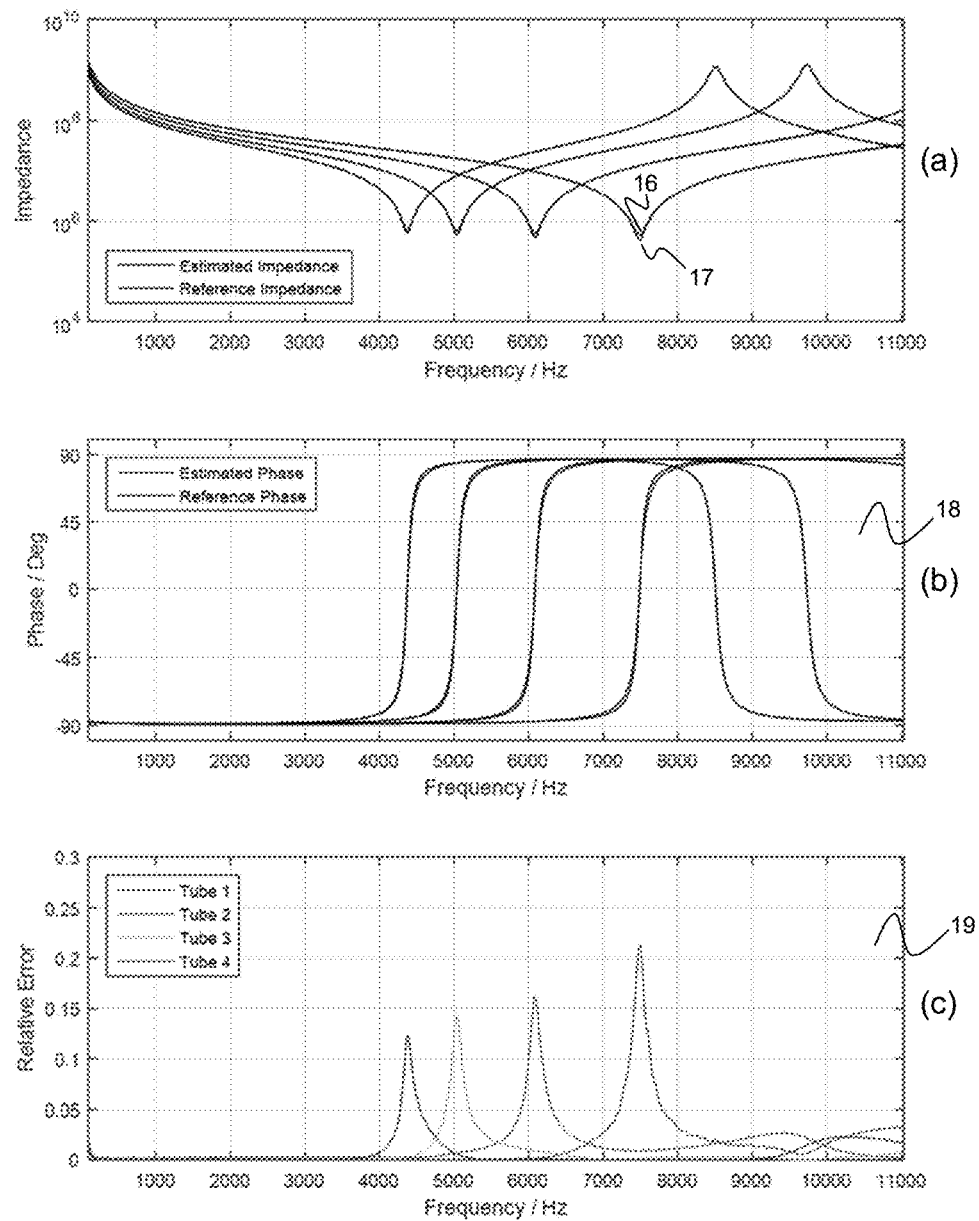
FIG. 3 shows similar results to those shown in FIG. 2 of a calibration using only the imaginary correction functions.
Figure 4:
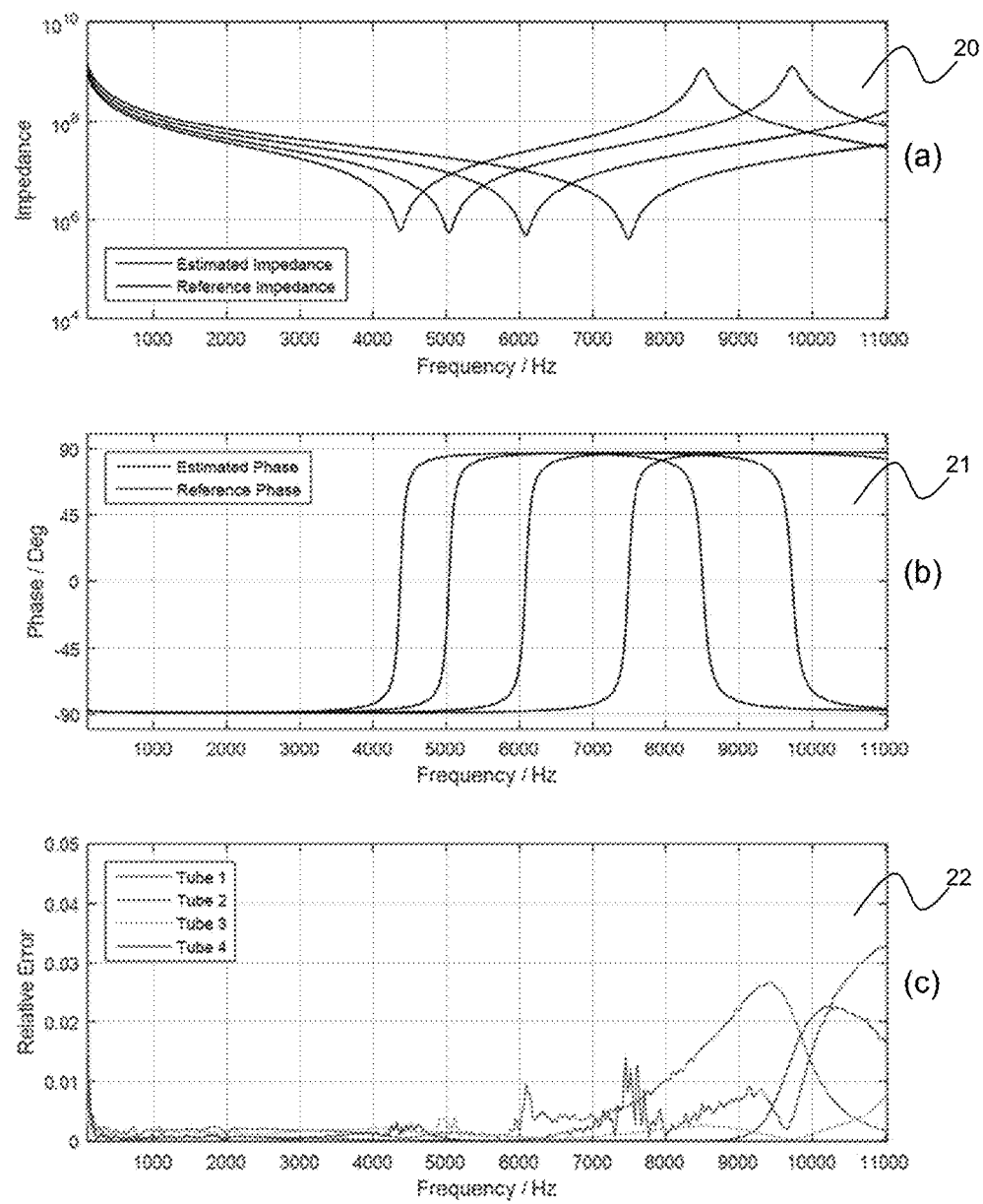
FIG. 4 shows similar results to those shown in FIG. 2 of a calibration in which both the real and imaginary correction functions are used.

The following FIGS. 2, 3 and 4 illustrate an example of the advantageous effect of applying the principles of the present disclosure. The results shown correspond to four different waveguides.

FIG. 2 shows results of a calibration without any correction functions being applied. FIG. 2(a) shows the magnitude of the estimated impedances 12 that are based on actual measurements for four different lengths of the waveguide compared with the corresponding reference impedances 11, FIG. 2(b) shows the phase of the estimated and corresponding reference impedances 14, 13, respectively and FIG. 2(c) shows the absolute value 15 of the relative error corresponding to each respective of the four applied waveguides. As it clearly appears from FIG. 2(c) a calibration without the application of any correction functions results in very large errors due to the geometrical mismatch between the probe and the waveguides. It is clearly seen from FIG. 2(a) that the geometrical mismatch between the acoustic probe and the waveguides introduces a substantial shift in the minima of the impedance measurement, which shift would lead to a significant error in the impedance if used without any correction.

According to the present disclosure, the large errors that result from the above mentioned mismatch are corrected for by the application of a complex frequency dependent correction factor $$\Delta Z(f) = \Delta Zre(f) + i\Delta Zim(f)$$

where f is the frequency and i is the imaginary unit. This correction is applied to the impedance measurements performed on the waveguides used for Thevenin calibration of the acoustic probe.

According to Fletcher et al. (2005) it was proposed to use the following real and imaginary part of the complex correction function $\Delta Z(f)$:

$$\Delta Zre(f) = Cre\sqrt{f}$$

and $$\Delta Zim(f) = iCimf$$

It is however expressly noted that the present disclosure is not restricted to the use of the above correction functions $\Delta Zre(f)$ and $\Delta Zim(f)$. Furthermore, it should also be noted that the method described in Fletcher et. al. does not focus on finding any source characteristics of the acoustic probe from a Thevenin calibration, which should be used for subsequent measurements. Rather, the method of Fletcher implies that such Thevenin calibration is performed in a first step, prior to any further impedance measurements. Thus, the correction for any geometrical mismatch is applied to a specific load having a specified geometry, whereby the correction factors found could substantially only be applied to a device of similar geometry and/or dimensions, as previously elaborated on.

On the contrary, the method described herein applies a complex correction factor already during the Thevenin calibration of the acoustic probe to be used for subsequent measurements. In this way it is ensured that the ratio between acoustic volume velocity at the speaker outlet of the probe and sound pressure at the microphone inlet used during calibration is modeled much more accurate instead of using simply the plane wave impedance. In contrast to Fletcher et al. subsequent impedance measurements of unknown acoustic loads will have all these effects included.

Referring now to FIG. 3 there are shown results of a calibration in which only the imaginary correction function $\Delta Zim(f)=iCimf$ is used. Each parameter is optimized for each waveguide to account for slight differences in probe insertion. FIG. 3(a) shows the magnitude of the estimated impedances 17 compared with the corresponding reference impedances 16, FIG. 3(b) shows the phase of the estimated and corresponding reference impedance and FIG. 3(c) shows the absolute value of the relative error 19 corresponding to each respective of the four applied waveguides. As it clearly appears from FIG. 3(c) the impedance minima are now aligned and the error significantly reduced, but the minima in the estimated impedances are deeper with more abrupt phase changes from −90 to +90 degrees. This indicates a difference in the amount of damping caused by the flow losses.

FIG. 4 shows results of a calibration where both the real and imaginary correction functions:

$$\Delta Zre(f)=Cre\sqrt{f}$$

and $$\Delta Zim(f)=iCimf$$

are used. FIG. 4(a) shows the magnitude 20 of the estimated and reference impedance, respectively (they are practically coincident in the figure), FIG. 4(b) shows the phase 21 of the estimated and reference impedance and FIG. 4(c) shows the absolute value 22 of the relative error corresponding to each respective of the four applied waveguides. As it clearly appears from FIG. 2(c) damping has been sufficiently accounted for and the error has dropped to an extremely low level.

The above examples clearly demonstrate the ability to drastically reduce errors in the estimated impedances already during the Thevenin calibration of the acoustic probe by applying a complex, frequency dependent correction factor to the reference impedances. It is expressly understood that the application of the specific correction functions shown above does only constitute an example, and that the scope of the present disclosure is not limited by this example.

With the method described herein, it should thus be understood that a correction of the errors introduced by a geometrical mismatch between the acoustic probe and any load applied thereto may be corrected for during calibration by minimizing the error of the calibration. Thereby the ratio of pressure on the probe microphone relative to volume velocity injected by the probe is modeled rather than the plane wave impedance. Subsequent impedance measurements, however, have these effects included and are thus not compensated with this method.

To sum up, the method therefore includes the steps of
providing an acoustic probe intended for use in impedance measurements of a device, instrument or other object of interest;
providing a set of waveguides with differences in geometry and with a known analytical impedance and/or a measured impedance of the waveguide
inserting the acoustic probe in each of the waveguides, and for each of the waveguides modeling the acoustic impedance, whereby to said modeled impedance (also denoted known or analytical impedance) a complex correction factor is added;
using the modeled impedance with the correction factors to solve for the Thevenin parameters (i.e. the source characteristic) of the acoustic probe used for the subsequent impedance measurements, where in each iterative step of finding of the correction factors for each waveguide, the Thevenin parameters are calculated by minimizing the least-square error function of the system to find the set of correction factors resulting in the lowest relative error of the calibration;
finally, using said corrected Thevenin calibration, any acoustic impedance may be measured as seen from the acoustic probe, which means that the potential effects of evanescent modes and flow losses are included in this measurement.

It should be noted that an initial guess for a complex correction factor may be applied to the model in order to speed up the calibration set-up.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:
1. A method comprising
carrying out acoustic Thevenin calibration of a probe or hearing aid, said probe or hearing aid comprising a measuring microphone and a sound emitting source, by presenting a plurality of different acoustic loads, one acoustic load at a time, to the output of the probe or hearing aid such that the sound emitting source and the measuring microphone of the probe or hearing aid are placed exactly flush with an input reference plane of each acoustic load when presented, while each of said acoustic loads is presented, emitting an acoustic stimulus via the sound emitting source and measuring a response via the measuring microphone, and calculating Thevenin parameters based on the measured responses and determined input impedances for said acoustic loads, respectively, said determined input impedance for said acoustic loads being calculated based on a known acoustic input impedance of said acoustic load and an additional frequency dependent complex correction factor $\Delta Z(f)$ corresponding to said acoustic load, and using said Thevenin parameters to calculate an impedance of an arbitrary acoustic load based on measurements obtained by said probe or hearing device from said arbitrary acoustic load, wherein said acoustic Thevenin calibration is used to determine the relationship between the sound pressure and the volume velocity at the input of the arbitrary acoustic load generated by the probe for a plurality of frequencies thereby obtaining source characteristics of the probe or a hearing aid, and wherein said frequency dependent complex correction factor $\Delta Z(f)$ for each of said acoustic loads is calculated in order to compensate for geometric mismatches between the probe and said acoustic load.

2. A method according to claim 1, wherein said loads are the input impedance of respective waveguides.

3. A method according to claim 1, wherein said known acoustic impedances are determined analytically.

4. A method according to claim 1, wherein said correction factors are adjusted individually for each waveguide in an iterative process;

whereby the lowest possible error and/or visual alignment of the graphs due to slight differences in insertion of the probe into the acoustic load resulting in variation of correction factors for each waveguide is obtained.

5. A method according to claim 4, wherein the number of iterative steps for the error to converge to a minimum is reduced by applying an initial value for both correction factors equal to an expected value for the specific probe and waveguide combination obtained from a previous calibration.

6. A method according to claim 1, wherein said frequency dependent complex correction factor $\Delta Z(f)$ is given by the expression:

$$\Delta Z(f)=\Delta Zre(f)+i\Delta Zim(f)$$

where:

$$\Delta Zre(f)=Cre\sqrt{f}$$

and $$\Delta Zim(f)=iCimf$$

7. A method according to claim 2, wherein said known acoustic impedances are determined analytically.

8. A method according to claim 2, wherein said correction factors are adjusted individually for each waveguide in an iterative process;

whereby the lowest possible error and/or visual alignment of the graphs due to slight differences in insertion of the probe into the acoustic load resulting in variation of correction factors for each waveguide is obtained.

9. A method according to claim 3, wherein said correction factors are adjusted individually for each waveguide in an iterative process;

whereby the lowest possible error and/or visual alignment of the graphs due to slight differences in insertion of the probe into the acoustic load resulting in variation of correction factors for each waveguide is obtained.

10. A method according to claim 2, wherein said frequency dependent complex correction factor $\Delta Z(f)$ is given by the expression:

$$\Delta Z(f)=\Delta Zre(f)+i\Delta Zim(f)$$

where:

$$\Delta Zre(f)=Cre\sqrt{f}$$

and $$\Delta Zim(f)=iCimf$$

11. A method according to claim 3, wherein said frequency dependent complex correction factor $\Delta Z(f)$ is given by the expression:

$$\Delta Z(f)=\Delta Zre(f)+i\Delta Zim(f)$$

where:

$$\Delta Zre(f)=Cre\sqrt{f}$$

and $$\Delta Zim(f)=iCimf$$

12. A method according to claim 4, wherein said frequency dependent complex correction factor $\Delta Z(f)$ is given by the expression:

$$\Delta Z(f)=\Delta Zre(f)+i\Delta Zim(f)$$

where:

$$\Delta Zre(f)=Cre\sqrt{f}$$

and $$\Delta Zim(f)=iCimf$$

13. A method according to claim 5, wherein said frequency dependent complex correction factor $\Delta Z(f)$ is given by the expression:

$$\Delta Z(f)=\Delta Zre(f)+i\Delta Zim(f)$$

where:

$$\Delta Zre(f)=Cre\sqrt{f}$$

and $$\Delta Zim(f)=iCimf$$

* * * * *